US012564382B2

(12) United States Patent
Waechter-Stehle et al.

(10) Patent No.: US 12,564,382 B2
(45) Date of Patent: Mar. 3, 2026

(54) 3D ULTRASOUND IMAGING WITH FOV ADAPTATION

(71) Applicant: KONINKLIJKE PHILIPS N.V., Eindhoven (NL)

(72) Inventors: Irina Waechter-Stehle, Hamburg (DE); Jochen Peters, Norderstedt (DE); Tanja Lossau, Hamburg (DE); Mathieu De Craene, Suresnes (FR); André Goossen, Eldena (DE); David Prater, Andover, MA (US); Jose Rivero, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/708,352

(22) PCT Filed: Nov. 8, 2022

(86) PCT No.: PCT/EP2022/081031
§ 371 (c)(1),
(2) Date: May 8, 2024

(87) PCT Pub. No.: WO2023/088715
PCT Pub. Date: May 25, 2023

(65) Prior Publication Data
US 2024/0415493 A1     Dec. 19, 2024

(30) Foreign Application Priority Data

Nov. 16, 2021   (EP) ..................................... 21290075

(51) Int. Cl.
*A61B 8/00*          (2006.01)
*G06T 7/149*        (2017.01)

(52) U.S. Cl.
CPC .............. *A61B 8/483* (2013.01); *G06T 7/149* (2017.01)

(58) Field of Classification Search
CPC ......... A61B 8/483; A61B 8/085; A61B 8/469; A61B 8/54; G06T 7/149;
(Continued)

(56) References Cited

U.S. PATENT DOCUMENTS

| | | |
|---|---|---|
| 5,997,479 A | 12/1999 | Savord et al. |
| 6,013,032 A | 1/2000 | Savord |

(Continued)

FOREIGN PATENT DOCUMENTS

| | | |
|---|---|---|
| CN | 106821416 A | 6/2017 |
| EP | 2575626 A1 | 4/2013 |

(Continued)

OTHER PUBLICATIONS

International Search Report and Written Opinion for PCT/EP2022/081031; Mailing date: Jan. 31, 2023, 11 pages.

*Primary Examiner* — Bo Joseph Peng

(57) ABSTRACT

A method is provided for adapting a 3D field of view (FOV) in ultrasound data acquisition so as to minimize the FOV volume in a manner that is controlled and precise. The method comprises defining a volumetric region across which 3D ultrasound data is desired, and then adapting the data acquisition field of view (FOV) in dependence upon the defined volumetric region, to encompass the region. This is achieved based on adapting a scan line length (or scan depth) of each individual scan line based on the defined volumetric region. In some embodiments, the volumetric region may be defined based on anatomical segmentation of a reference ultrasound dataset acquired in an initial step, and setting the volumetric region in dependence upon boundaries of an identified object of interest. The volumetric region may in a (Continued)

subset of embodiments be set as the region occupied by a detected anatomical object of interest.

17 Claims, 6 Drawing Sheets

(58) Field of Classification Search
CPC . G06T 2207/10136; G06T 2207/20132; G06T
2207/30048; G06T 7/12; G01S 15/8915;
G01S 7/52063; G01S 15/8925; G01S
15/8993
See application file for complete search history.

(56) References Cited

U.S. PATENT DOCUMENTS

| | | | |
|---|---|---|---|
| 6,056,691 | A | 5/2000 | Urbano et al. |
| 6,283,919 | B1 | 9/2001 | Roundhill et al. |
| 6,443,896 | B1 | 9/2002 | Detmer |
| 6,458,083 | B1 | 10/2002 | Jago et al. |
| 6,530,885 | B1 | 3/2003 | Entrekin et al. |
| 6,623,432 | B2 | 9/2003 | Powers et al. |
| 2004/0199077 | A1 * | 10/2004 | Hao ..................... G06T 7/0012<br>600/443 |
| 2009/0105585 | A1 * | 4/2009 | Wang ................... A61B 8/4455<br>600/437 |
| 2010/0056923 | A1 | 3/2010 | Hyun et al. |
| 2010/0094606 | A1 * | 4/2010 | Richard .............. G01N 29/262<br>703/2 |
| 2011/0172532 | A1 | 7/2011 | Yoo et al. |
| 2016/0262720 | A1 | 9/2016 | Henderson et al. |
| 2021/0100526 | A1 * | 4/2021 | Schein ................ A61B 8/5215 |
| 2023/0186477 | A1 * | 6/2023 | Gilbert ..................... G06T 7/11 |
| 2023/0267618 | A1 * | 8/2023 | Gogna .................. G16H 30/40<br>382/131 |

FOREIGN PATENT DOCUMENTS

| | | | |
|---|---|---|---|
| EP | 3649959 | A1 | 5/2020 |
| EP | 3711673 | A1 | 9/2020 |
| WO | 2019076659 | A1 | 4/2019 |

* cited by examiner

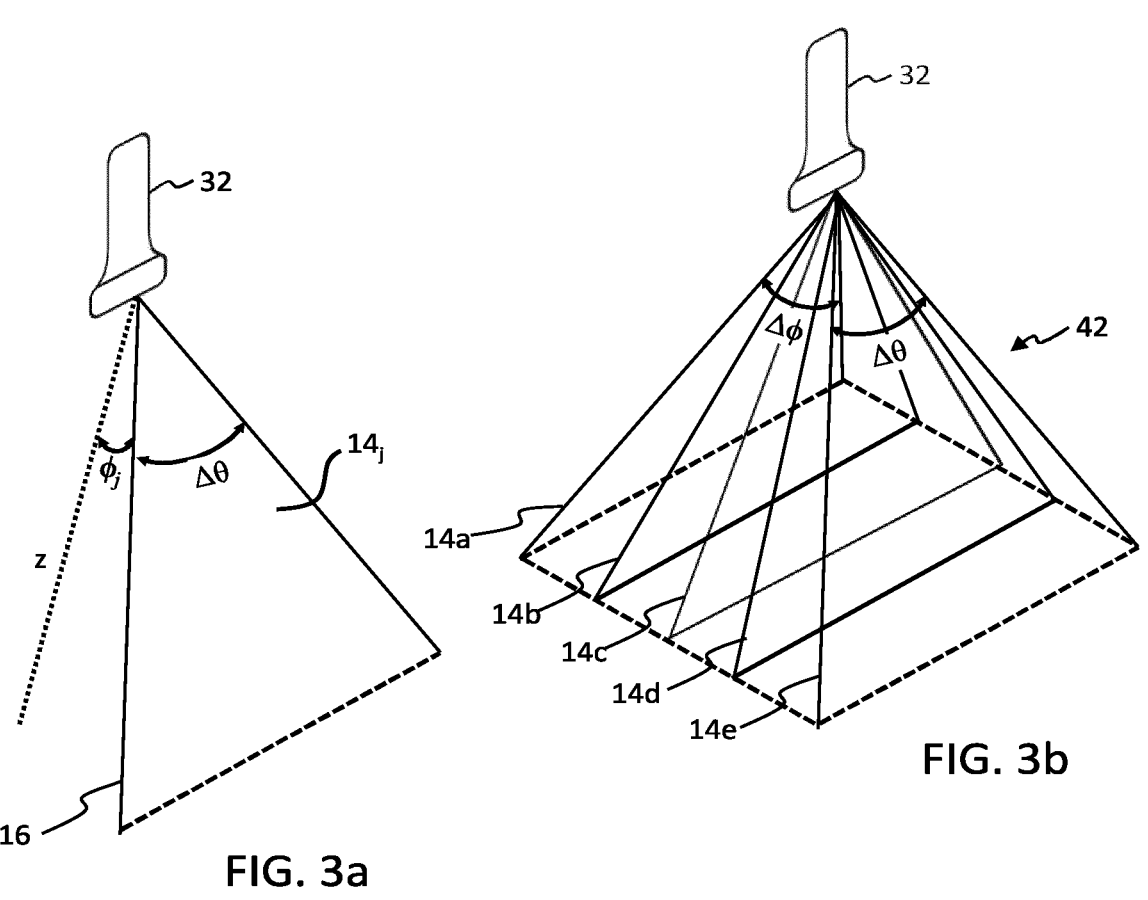
FIG. 3a
FIG. 3b
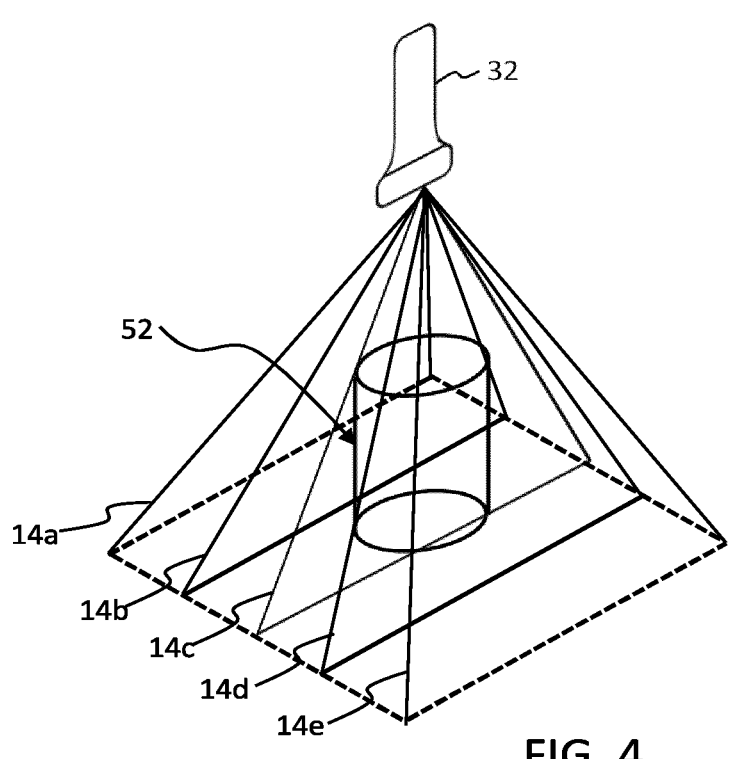
FIG. 4

3D ULTRASOUND IMAGING WITH FOV ADAPTATION

CROSS-REFERENCE TO PRIOR APPLICATIONS

This application is the U.S. National Phase application under 35 U.S.C. § 371 of International Application No. PCT/EP2022/081031, filed on Nov. 8, 2022, which claims the benefit European Patent Application No. 21290075.7, filed on Nov. 16, 2021. These applications are hereby incorporated by reference herein.

FIELD OF THE INVENTION

The present invention relates to a method for acquiring 3D ultrasound image data with an adapted FOV.

BACKGROUND OF THE INVENTION

Three-dimensional (3D) ultrasound data acquisition (or volumetric ultrasound) is a developing technological field.

One useful application for 3D ultrasound is for imaging the heart, since it allows for more accurate observation of heart structures, such as heart chambers and heart valves. 3D ultrasound however can usefully be applied to the imaging of any anatomical region or structure.

Four-dimensional (4D) ultrasound data acquisition comprises the acquisition of a temporal series of 3D ultrasound imaging frames.

The acquisition of 4D ultrasound data encompasses a trade-off between 3D spatial resolution, temporal resolution, and the size of the 3D field of view (FOV). For a fixed temporal resolution (i.e. frames per second), then a larger 3D FOV means reduced spatial resolution within each 3D frame and vice versa. Likewise, for a fixed FOV size, increased temporal resolution necessitates a reduced spatial resolution.

Thus, in most instances, in order to ensure that the required anatomical object or region is fully captured in the FOV, the FOV size is kept relatively large meaning that temporal resolution or spatial resolution has to be reduced. The FOV captured by a 3D ultrasound scan is typically either a cone shape or pyramid shape emanating from the ultrasound emission source. Reducing the size of the cone or pyramid risks cutting off part of the object being imaged.

For example, in cardiac imaging, often parts of the heart are cut off, either at the apex, at the lateral wall, or at the right ventricle. If the acquisition is wide enough to cover the complete heart, the frame rate is consequently quite low.

This frame rate not only affects diagnostic capability of the clinician, but also impacts on the accuracy of automated segmentation and quantification algorithms applied to the data for identifying anatomical object dimensions, and determining physiological parameters (e.g. hemodynamic parameters in the case of cardiac imaging). Such algorithms and models require high frame rate, e.g. in the case of 3D coronary artery disease detection by regional wall motion analysis. In current clinical setups, in order to achieve the required frame rate, 2D imaging must be used instead of 3D. Several 2D sequences are acquired with high frame rate (e.g. ~50 Hz). The sonographer then has to mentally compile or amalgamate these 2D results to make a diagnosis since, in principle, motion abnormality analysis is a 3D problem. This stitching process is complex and might lead to misinterpretations.

It is an aim to find a technical solution to address one of more of the above-identified problems.

SUMMARY OF THE INVENTION

The invention is defined by the claims.

In accordance with an aspect of the invention, there is provided a computer-implemented method. The method comprises obtaining reference 3D ultrasound data of an anatomical region for a first 3D FOV, wherein the reference ultrasound data comprises data for a series of scan lines, each scan line having a scan angle relative to a first ($\phi$) and second ($\theta$) angular scan direction, and maximum scan depth (d) along a direction of the scan line.

The method further comprises defining a volumetric region within the anatomical region, the volumetric region having one or more boundaries.

The method further comprises adjusting one or more scanning parameters to acquire new 3D ultrasound data with an adjusted 3D FOV, wherein adjusting the scanning parameters is performed in dependence upon the boundaries of the volumetric region, and wherein the adjusted 3D FOV fully encompasses the volumetric region, and wherein adjusting the scanning parameters comprises adjusting the maximum scan depth (d) of each individual scan line.

The method further comprises acquiring new 3D ultrasound data for the adjusted 3D FOV using the adjusted scanning parameters.

Thus the method is based on modifying individual scan line depths (or lengths) so as to enable acquisition of an arbitrarily shaped and sized 3D FOV. This allows for the 3D FOV to be reduced in size in a more controlled and directed way, so that risk of missing part of the anatomy of interest is reduced. For example, the adjusting the maximum scan depth (d) of each individual scan line may comprise adjusting a time duration of a receive phase of a transmit/receive sequence of one or more transducers used to acquire the relevant scan line.

As result, in the context of 4D imaging, the frame rate can be increased. This may improve the quality of results derived from automated quantification operations, which determine physiological parameters from ultrasound image data. It may also enable new applications, such as analysis of regional wall motion abnormalities in 3D, where a high frame rate is required.

The volumetric region may be a smaller 3D volume than the whole anatomical region covered by the reference scan. Therefore, it can be acquired in less time. The acquisition is enabled through controlling the scan depth of each individual scan line to match the desired 3D FOV. This ensures that the relevant anatomical sub-region is captured (where the region this could be user-defined, or automatically detected through segmentation).

Scan line depth means a depth along a direction of the scan line, i.e. along an axis parallel to the propagation path of the scan line through the body. In other words scan line depth in this context means the same as scan line length. The scan line depth is adjustable through control of acquisition or transmission parameters (i.e. drive parameters of the transducer array). Thus, the scan line depth is adjusted at the level of the transducers (rather than for example being adjusted through post-processing of acquired ultrasound signal data). In this way, acquisition speed can be improved, by limiting the scan line depth to only that needed for acquiring the volumetric region.

In particular, most commonly the scan line depth is controlled by controlling the time duration of the receive phase of the transmit/receive sequence of the relevant transducer(s) used to acquire the relevant scan line.

There are different ways that the region to be covered by the adapted FOV can be defined. It can be defined manually, for example using user input. It can be defined according to a pre-configured control scheme. In further examples, it can be defined automatically using anatomical image analysis applied to the reference image data. In all cases, the technical effect of reducing the total spatial volume over which data needs to be acquired is achieved, and this is achieved through modifying the FOV at the level of each individual scan line: adapting each scan line length so as to capture a 3D FOV having arbitrarily customizable boundaries.

In some cases, the adjusted FOV may have a set of boundaries which coincide with at least a subset of boundaries of the defined volumetric region.

In some (though not all) embodiments, the method comprises applying anatomical segmentation, and wherein the volumetric region is defined in dependence upon the anatomical segmentation.

There are different ways of controlling the scan parameters so as to enable to acquisition of the adjusted FOV, and these are now briefly outlined.

In at least one set of embodiments, the scan parameters are adjusted such as to define a set of scan lines having scan depths set such that each scan line terminates at a point of intersection of the scan line with a distal-most one of the one or more boundaries of the defined volumetric region. Distal-most means furthest along the length of scan line from the ultrasound emission source. All of the scan lines may be set in this way or just a portion. For instance, just the set of scan lines which coincide with the volumetric region may be set in this way.

As a variation on this, in some embodiments, the method may comprise defining a termination point for each scan line depth based on, for each scan line, identifying the line depth (or length) to the detected point of intersection with the boundary of the volumetric region, and adding a defined margin to this intersection depth, and setting the line depth for the adjusted FOV equal to this depth with the margin added. This allows for a certain margin or spacing around the volumetric region, in the depth direction.

The method may further comprise identifying a subset of scan lines which do not intersect with the defined volumetric region, and wherein the scan lines which do not intersect are deactivated when scanning the adjusted FOV. Deactivated means that, in acquiring ultrasound data for the adjusted 3D FOV, these scan lines are not generated/fired.

In some cases, all of the scan lines which do not intersect with the volumetric region are deactivated. In a variation on this, in some embodiments, a portion of the non-intersecting scan lines may be retained, for example to capture a predefined margin or spacing region around the volumetric region, as will be explained more later.

The scan lines in each of the reference and new 3D ultrasound data may be understood to span each of a series of 2D planes, wherein the series of 2D planes together span the respective 3D FOV across the first angular direction ($\phi$), and the scan lines forming each plane span the plane across the second angular direction ($\theta$), and wherein each 2D scan plane has an angular orientation along said first angular direction.

In some embodiments, adjusting the scan parameters may comprise:

adjusting for each individual 2D scan plane, a maximum angular width ($\Delta\theta$) along the second angular direction spanned by the scan lines in the 2D plane, and adjusting a maximum angular width ($\Delta\phi$) along the first angular direction spanned by the series of scan planes.

Scan lines outside of the maximum angular width are deactivated.

The maximum angular widths may be set in dependence upon the boundaries of the identified volumetric region.

In some cases, the maximum angular width ($\Delta\theta$) for each plane is set to the minimum width required for said plane to fully encompass the boundaries of the volumetric region. The same might also be applied for the maximum angular width ($\Delta\phi$) along said first angular direction spanned by the series of scan planes. In this case, the adjusted 3D FOV is sized to just encompass the desired volumetric region.

In other examples, the maximum angular width ($\Delta\theta$) for each plane is set to a sum of: the minimum width required for said plane to fully encompass the boundaries of the volumetric region, and a defined angular margin. The same may also be applied for the maximum angular width ($\Delta\phi$) along said first angular direction spanned by the series of scan planes.

The 2D planes are elevational planes.

In some examples, each 2D plane of ultrasound data may be acquired by sequentially firing a series of scan lines at sequentially incrementing or decrementing scan angles along the second angular direction $\theta$ relative to the transducer arrangement, and wherein all the lines lay in said same plane. This process is then repeated sequentially for a series of planes, and wherein each plane has an angle of orientation along said first angular dimension $\phi$ relative to the z-axis.

The planes may typically be triangular or truncated triangular, where the angular width of the plane means the angle of the apex of the plane.

In accordance with any of the above-described approaches, in some cases, the adjusted 3D FOV may include a subset of scan lines which do not intersect the volumetric region (e.g. when a margin or spacing is desired around the volumetric region). In these cases, optionally, the maximum scan depth for said subset of scan lines is set based on a scan depth which has been set for a nearest scan line which does intersect the object of interest.

Nearest may mean angularly nearest, i.e. the intersecting line whose scan angle $\theta$, $\phi$ is closest to the respective non-intersecting scan line.

There are different approaches to defining the volumetric region. In some embodiments, it may be defined manually, e.g. through user input. In some cases, it may be predetermined. In a preferred set of embodiments, it is defined in dependence upon a result of an automated anatomical segmentation procedure applied to the reference ultrasound data.

Thus, in accordance with at least one set of embodiments, the method comprises applying segmentation to the reference 3D ultrasound data to detect boundaries of an anatomical object-of-interest in the reference 3D ultrasound data; and defining the volumetric region within the anatomical region in dependence upon the detected boundaries of the anatomical object-of-interest. In particular, the volumetric region may be defined so as to fully contain the detected boundaries of the anatomical object of interest.

Within this set of embodiments, there are further options for how the volumetric region is defined based on the segmentation.

For example, in a simple case, the boundaries of the detected anatomical object-of-interest are simply used as the boundaries of the volumetric region. In other words, the boundaries of the volumetric region are set so as to match the detected boundaries of the anatomical object of interest.

As a variation on this, the boundaries of the volumetric region may instead be defined so as to fully contain the detected boundaries of the anatomical object of interest in addition to a pre-defined spacing or margin around the boundaries of the object of interest, for instance for accommodating motion of the object.

In some embodiments, defining the volumetric region may comprise defining a 3D shape for the volumetric region, and defining a scale size of said shape which is the minimum able to accommodate the boundaries of the anatomical object of interest, and optionally in addition to a defined spacing around the boundaries.

Here, defining the 3D shape of the volumetric region may comprise: defining the shape according to a pre-defined shape template (for example a cylinder, a cuboid, an ellipsoid, a pyramid, a truncated or frustrated pyramid, an elliptical cylinder, or any other shape), or may comprise determining a custom shape based on the detected boundaries of the object. In the latter case for example, defining the shape may comprise determining a custom shape based on the detected boundaries of the object, and wherein the custom shape is a convex hull. In some cases for example, detecting the boundaries of the anatomical object may comprise detecting segmentation mesh vertex points which span the boundaries of the object, or may comprise detecting voxels which span the boundaries of the object, and wherein the convex hull is defined to connect said vertex points or voxels.

As mentioned, in some cases, the volumetric region is defined to include a spacing around the object of-interest for accommodating movement. Determining the spacing could in some cases be performed automatically based on the reference ultrasound data. In particular, if the reference ultrasound data is 4D ultrasound data (i.e. comprising a series of frames of 3D ultrasound data), then in cases where the volumetric region is defined so as to fully contain the detected boundaries of the anatomical object of interest in addition to a pre-defined spacing around the object boundaries, in some embodiments, an extent of said spacing around the boundaries may be determined based on detecting a maximal extent of the object-of-interest boundary across the series of frames.

A further aspect of the invention provides a computer program product comprising code means configured, when executed on a processor which is communicatively coupled with an ultrasound imaging apparatus, to cause the processor to perform a method in accordance with any embodiment or example outlined in this disclosure, in accordance with any claim of this application.

Another aspect of the invention provides a processing arrangement comprising: an input/output, for two-way communication with an ultrasound imaging apparatus, and one or more processors.

The one or more processors are adapted to perform at least the following steps:

obtain at the input/output reference 3D ultrasound data of an anatomical region for a first 3D FOV, wherein the reference ultrasound data comprises data for a series of scan lines, each scan line having a scan angle along a first ($\phi$) and second ($\theta$) angular scan direction, and maximum scan depth (d) along a direction of the scan line;

define a volumetric region within the anatomical region, the volumetric region having one or more boundaries;

adjust one or more scanning parameters to acquire new 3D ultrasound data with an adjusted 3D FOV, wherein adjusting the scanning parameters is performed in dependence upon the boundaries of the volumetric region, and wherein the adjusted 3D FOV fully encompasses the volumetric region, and wherein adjusting the scanning parameters comprises adjusting the maximum scan depth (d) of each individual scan line; and communicate the adjusted scanning parameters to the ultrasound imaging apparatus to cause the apparatus to acquire new 3D ultrasound data for the adjusted 3D FOV using the adjusted scanning parameters.

A further aspect of the invention provides a system comprising an ultrasound imaging apparatus; and a processing arrangement in accordance with any embodiment of examples outlined in this disclosure, or in accordance with any claim of this application. The processing arrangement is communicatively coupled with the ultrasound imaging apparatus for receiving ultrasound image data and for communicating the adjusted scanning parameters to the ultrasound imaging apparatus. These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 2 illustrates the geometry of acquisition scan lines and scan planes;

FIG. 3 illustrates the acquisition of a 3D field of view (FOV);

FIG. 4 illustrates an example volumetric region defined within a first FOV;

DETAILED DESCRIPTION OF THE EMBODIMENTS

Figures 1, 2A, 2B, 2C:
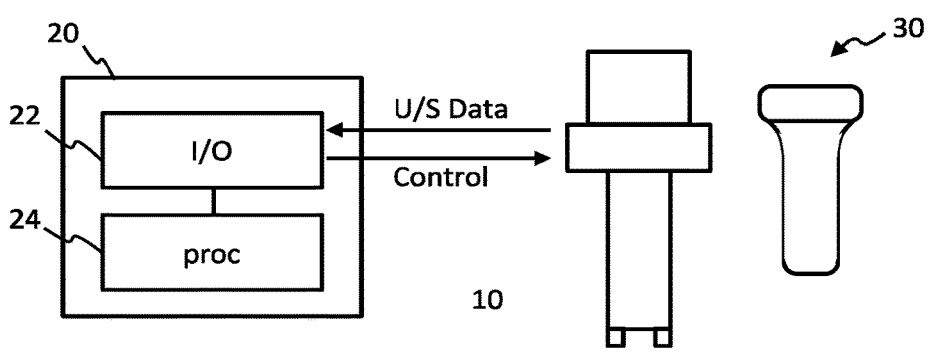
FIG. 1 shows an example system and processing arrangement according to one or more embodiments of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for adapting a 3D field of view (FOV) in ultrasound data acquisition so as to minimize the FOV volume in a manner that is precisely controllable. The method comprises defining a volumetric region across which 3D ultrasound data is desired, and then adapting the data acquisition field of view (FOV) in dependence upon the defined volumetric region, to encompass the region. This is achieved based on adapting a scan line length (or scan depth) of each individual scan line based on the defined volumetric region. In some embodiments, the volumetric region may be defined based on anatomical segmentation of a reference ultrasound dataset acquired in an initial step, and setting the volumetric region in dependence upon boundaries of an identified object of interest. The volumetric region may in a subset of embodiments be set as the region occupied by a detected anatomical object of interest.

As aspect of the invention provides a computer implemented method as will be described below.

The computer-implemented method can be implemented by a processing arrangement, and a processing arrangement adapted to perform the method forms another aspect of this invention.

In implementing the method, the processing arrangement may be operatively coupled with an ultrasound imaging apparatus for acquisition of ultrasound data. A system which comprises the processing arrangement and the ultrasound imaging apparatus together also forms another aspect of this invention. The system may include further components such as a user interface comprising a display, which may be controlled to display a rendering of acquired ultrasound imaging data.

By way of illustration. FIG. 1 schematically outlines an example system 10 in accordance with one or more embodiments of the invention. The system comprises a processing arrangement 20. The processing arrangement comprises an input/output (I/O) 22, for two-way communication with an ultrasound imaging apparatus 30, and further comprises one or more processors ("proc") 24. The one or more processors are adapted to implement a method as will be outlined below. The system 10, the processing arrangement 20 and the method described below each may be provided independently as a respective aspect of the invention.

The computer-implemented method in accordance with one or more embodiments comprises, in summary, at least the following steps:

obtaining reference 3D ultrasound data of an anatomical region for a first 3D FOV 42;

defining a volumetric region 52 within the anatomical region, the volumetric region having a set of one or more boundaries;

adjusting one or more scanning parameters to acquire new 3D ultrasound data with an adjusted 3D FOV 44, wherein adjusting the scanning parameters is performed in dependence upon the boundaries of the volumetric region, and wherein the adjusted 3D FOV fully encompasses the volumetric region, and wherein adjusting the scanning parameters comprises adjusting the maximum scan depth, d, of each individual scan line; and acquiring new 3D ultrasound data for the adjusted 3D FOV using the adjusted scanning parameters.

Adjusting the scanning parameters comprises adjusting a maximum scan depth (d) of each individual scan line. For example it may comprise, for at least a subset of the scan lines, adjusting a maximum scan depth of the line in dependence upon a detected point of intersection between a distal-most (along a direction of the line from the ultrasound source) boundary of the volumetric region. For example, in some cases, a terminal end point of each scan line is set to coincide with said detected point of intersection. For some scan lines, the line depth may be set to zero (i.e. the line is deactivated or not generated at all).

The reference 3D ultrasound data may be obtained passively, for example it is received at the input/output of the processing arrangement from an ultrasound imaging apparatus which has acquired it. Alternatively, the method may comprise actively controlling an ultrasound transducer arrangement comprised by the imaging apparatus to acquire the data, or may issue one or more control instructions to the ultrasound imaging apparatus to cause the imaging apparatus to acquire the reference ultrasound imaging data.

The method is further illustrated by FIGS. 2-7, which illustrate acquisition of ultrasound data with an ultrasound transducer unit 32 comprising an ultrasound transducer arrangement 34 which provides a source of ultrasound emissions.

With reference, to FIGS. 2-7, both the aforementioned reference 3D ultrasound data, and the new 3D ultrasound data, can be understood as comprising data for a series of scan lines 16 spanning each of a series of elevational 2D planes 14. The series of elevational 2D planes together span the first 3D FOV 42 across a first angular direction, $\phi$(see FIG. 3$b$), and the scan lines forming each plane span the plane across a second angular direction, $\theta$ (FIG. 2$a$). Each 2D scan plane 14$_j$ thus has an angular orientation $\phi_j$ along said first angular direction. The second angular direction. $\theta$, is orthogonal to the first angular direction, $\phi$. Each scan line 16$_i$ can be fully defined by a scan line angle ($\phi_i$, $\theta_i$) defining its angular direction from the ultrasound source relative to each of the first $\phi$ and second $\theta$ angular directions. Each scan line also has a maximum scan depth, d$_i$, along a direction of the scan line. Within each given scan plane 14$_j$, the scan lines 16$_i$ all have the same scan angle in the first angular direction $\phi$, equal to the orientation of the respective plane $\phi_j$, and vary in orientation across the plane 14 in the second angular direction $\theta$ (FIG. 2$b$).

Each 2D scan plane 14$_j$ has a maximum angular width, $\Delta\theta$, along said second angular direction, spanned by the scan lines 16 in the scan plane (see e.g. FIG. 3$b$).

The complete 3D FOV furthermore has a maximum angle, $\Delta\phi$, along said first angular direction spanned by the series of scan planes (see FIG. 3$b$)

The first $\phi$ and second $\theta$ angular dimensions may be defined relative to a central z axis, or a central origin, where the origin centers on the source of the ultrasound emissions (i.e. the transducer arrangement 32).

FIG. 2$a$ illustrates how each 2D plane 14$_j$ of data may be formed by sequentially generating a series of scan lines 16$_i$ which span an angular width $\Delta\theta$ of the plane across the second angular dimension $\theta$. Each plane of ultrasound data is acquired by sequentially firing the scan lines at sequentially incrementing or decrementing scan angles, $\theta_i$, along the second angular direction $\theta$) relative to the transducer arrangement 34, and all the scan lines lying in said same plane 14. In this way, the data for the full plane is sequentially compiled, one scan line at a time. As shown in FIG. 3$b$, this process is then repeated sequentially for a series of planes 14$_j$, and wherein each plane has an angle of orientation $\phi_j$ along said first dimension $\phi$ relative to the z-axis (see FIG. 3a). FIG. 2a is schematic only, and more scan lines or fewer scan lines may in practice be used.

FIG. 2b schematically illustrates for a single example scan line $16_i$ the scan angle, $\theta_i$, of the scan line along the second angular direction $\theta$, and the scan depth $d_i$ of the scan line along the direction of the line. The scan depth of each individual scan line is individually adjustable for example through control of the time duration of the receive phase of the transmit/receive sequence of the relevant transducer(s) used to acquire the relevant scan line. In particular, a scan line is acquired with a transmit/receive sequence in which an ultrasound pulse signal is transmitted from the transducer, and immediately following this, the same transducer or an adjacent transducer begins sensing or sampling the returning echo of the transmitted signal (the echo signal) for a certain sampling time window, which may be referred to as the receive phase window. By controlling the time duration of the receive phase time window, the depth to which the echo signal is sampled is controlled, since later received echo signal portions correspond to deeper locations within the body from which the echo signal portion has back-reflected. Thus, in this way, the scan depth of each scan line can be individually controlled, by controlling the corresponding transducer receive phase time window.

In more detail, the control of the transmit/receive sequences of the transducers may be implemented with a timing table that controls the length of each scan line. Each line effectively begins with a transmit pulse. A few microseconds after the transmit pulse, the returning echoes start to be received back from the body for that line. The scan line effectively terminates when the system ceases to measure or sample the returning echo signals. If the same transducer is used both for transmission and sensing (in alternating duty cycles), then a scan line effectively ends when the transmit pulse for the next line is generated. Therefore, controlling the scan depth of each scan line may in practice comprise configuring the timing table which controls the transmit/receive phase timings for each scan line, and this could be configured by a controller of the system.

FIG. 2c schematically illustrates for a single example 2D scan plane $14_j$ the maximum angular width $\Delta\theta$ of the plane across the second angular direction $\theta$).

FIG. 3a illustrates for a single example 2D scan plane $14_j$ the angle of orientation $\phi_j$ of the plane along said first dimension $\phi$ relative to the z-axis.

FIG. 3b schematically illustrates acquisition of a full volumetric dataset covering a 3D FOV within an anatomical region by sequentially acquiring data across a series of 2D scan planes $14a$-$14c$, where the series of scan planes together span a maximum angular width $\Delta\phi$ across the first directional dimension $\phi$. Although five planes 14 are shown in FIG. 3b, more or fewer planes may in practice form the 3D FOV.

For purposes of illustration, the 3D FOV shown in FIG. 3b is taken to be the first 3D FOV 42 referred to previously, the ultrasound data for which forms the reference ultrasound data referred to previously. In this example, the first 3D is taken to have a standard FOV geometry (e.g. using a cone or pyramid shaped geometry) which for example spans the maximum possible angular width in both the first $\phi$ and second $\theta$ directions, and in which each plane $14_i$ has identical shape. In other words it is the full possible FOV. However, this is not essential.

FIG. 4 illustrates defining an example volumetric region 52 within the anatomical region covered by the first 3D FOV 42. In this example, the volumetric region 52 is a sub-region of the volume spanned by the first 3D FOV 42, i.e. it defines smaller volume than the first 3D FOV. However, this is not essential, and the volumetric region could be larger than the first 3D FOV.

The first 3D FOV 42 acts for example as a survey scan, which may be used to inform the defining of the volumetric region 52.

In the illustrated example, the volumetric region 52 is set simply as a pre-defined geometrical shape—in this case a cylinder. However, as will be explained in detail further below, in other examples, the shape of the volumetric region can be defined arbitrarily, and could have any regular or irregular 3D geometry. The volumetric region 52 may be manually defined, e.g. via user input, may be pre-defined, e.g. by a pre-set control scheme, or (as will be discussed in detail late) may be automatically defined based on anatomical image analysis applied to the reference image data. For example, the method may comprise applying segmentation to the reference 3D ultrasound data and the volumetric region may be defined in dependence upon boundaries of an identified anatomical object-of-interest obtained from the segmentation. The boundaries of the volumetric region may simply be set as the boundaries of the identified object, or it may be set differently, e.g. as a shape which encompasses the boundaries of the anatomical object, plus some margin or spacing.

Once the volumetric region 52 is defined, one or more scanning parameters are adjusted to acquire new 3D ultrasound data with an adjusted 3D FOV 44 having boundaries set in dependence upon the boundaries of the volumetric region 52. The adjusted 3D FOV should at least fully encompass the volumetric region.

There are at least two main approaches to doing this.

The first is to identify the subset of the scan lines $16_i$ which intersect with at least one boundary of the volumetric region 52: identify the point of intersection of each of the identified subset of scan lines with a boundary of the defined volumetric region; and then adjust each respective scan line $16_i$ depth, $d_i$, such that a terminal point of the scan line coincides with the identified point of intersection for the scan line, and preferably wherein the boundary is a distal-most boundary of the volumetric region along the direction of the scan line. Remaining non-intersecting scan lines 16 are deactivated (in other words, when scanning the adjusted FOV to acquire the new ultrasound data, the non-intersecting scan lines are not generated/fired). This results in an adjusted FOV which has boundaries which at least partially match or map onto boundaries of the volumetric region.

In a variation to this approach, instead of setting of the scan line $16_i$ depths, $d_i$, so that the scan line terminates at the aforementioned point of intersection, the scan line termination point may instead be set based on, for each scan line, identifying the line depth/length to the point of intersection, and adding a defined margin to this intersection depth, and then setting the line depth for the adjusted FOV equal to this depth with the margin added. This optionally allows for the adjusted FOV to include a spacing or margin around the volumetric region in the line depth direction.

The second approach is similar to the first except that, instead of simply deactivating scan lines which do not intersect with the volumetric region, instead the method comprises a step of determining a maximum scan width $\Delta\theta$ of each scan plane $14_j$ in the second angular direction, and a maximum scan width $\Delta\phi$ spanned by the collection of planes 14 across the first angular direction, and where these are determined in dependence upon the identified boundaries of the volumetric region 52. This allows for greater flexibility and control in the size and geometry of the adjusted FOV relative to the volumetric region 52 of interest. This optionally allows for example, for inclusion within the adjusted FOV of scan lines which do not intersect with the volumetric region, for instance to allow for a certain spacing or margin around the volumetric region. Thus, in particular, for each plane 14$_j$: the maximum angular width, $\Delta\phi$, may be set to the minimum width required for said plane to fully encompass the boundaries of the volumetric region 51: or the maximum angular width may be set to a sum of: the minimum width required for said plane 14$_j$ to fully encompass the boundaries of the volumetric region, and a defined angular margin or spacing. Scan lines 16 outside of the maximum angular widths are deactivated. The same may also be applied for setting the maximum angular width. $\Delta\phi$, along said first angular direction spanned by the series of scan planes.

Determining the minimum angular widths $\Delta\theta$, $\Delta\phi$, to fully encompass boundaries of the volumetric region can be done by identifying, within the same co-ordinate system used to define the scan lines 16 and scan places 14, angular co-ordinates of points which lie on the boundaries (e.g. boundary surfaces) of the volumetric region, and then identifying the maxima among these points, for example maximum angular position among these points in each of the first $\phi$ and second $\theta$ angular directions.

To illustrate further, an example is considered below in which it is desired that the adjusted FOV be set so that its boundaries at least partially match or map onto the boundaries of the volumetric region (i.e. without a spacing or margin).

To achieve this, the scan depth of each scan line 16$_i$ in each scan plane 14$_j$ is individually adjusted, to set the scan depth equal to an identified point of intersection of the respective scan line with an outer boundary of the volumetric region 52. Thus the method may comprise a step, after defining the volumetric region, of determining a point of intersection of each scan line with an outer boundary of the defined volumetric region, and setting the scan line depth of each line so that the scan line terminates at said point of intersection. In this way, the adjusted FOV 44 will have a 3D shape that at least partially matches the 3D shape of the defined volumetric region 52. If the scan line coincides with more than one boundary of the volumetric region, its depth may be set to terminate at a point of intersection with the boundary of the volumetric region which is at the furthest distance along its length from the ultrasound source, i.e. the distal-most boundary.

Figure 5:
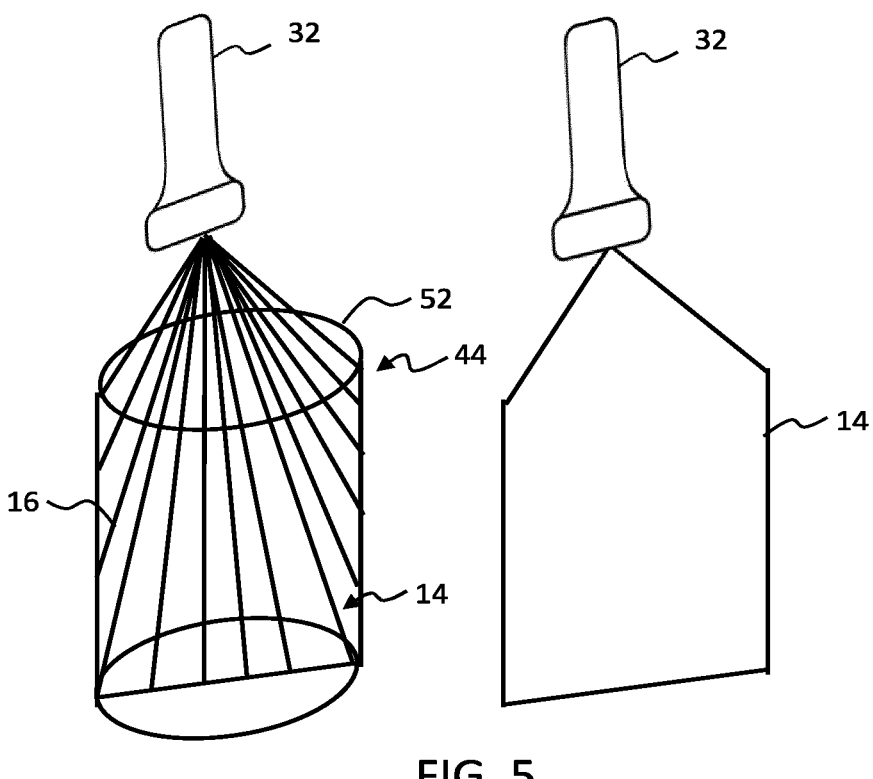
FIG. 5 illustrates acquisition of scan data for one plane within an adjust FOV, the adjusted FOV having boundaries set in dependence upon boundaries of the defined volumetric region.

To illustrate further. FIG. 5 schematically illustrates the acquisition of a single plane 14$_j$ of data within the adjusted FOV 44. As shown, the scan depth of the scan lines 16 in the plane have each been individually adjusted so that they terminate at a point of intersection with the outer boundary of the volumetric region. The resulting scan plane 14$_j$ has a shape defined by a set of outer boundaries, and wherein a subset of these boundaries coincide with a subset of the boundaries of the volumetric region 52. The plane also has further boundaries extending from the ultrasound source, and span the area of scan line propagation toward the volumetric region from the ultrasound source. The total resulting adjusted 3D FOV 44 will likewise comprise a set of outer boundaries, a subset of which coincide with the boundaries of the volumetric region 52. In particular, the distal-most boundaries of the volumetric region along directions of ultrasound propagation from the ultrasound source will coincide with distal-most boundaries of the adjusted 3D FOV along said directions of propagation.

Figure 6:
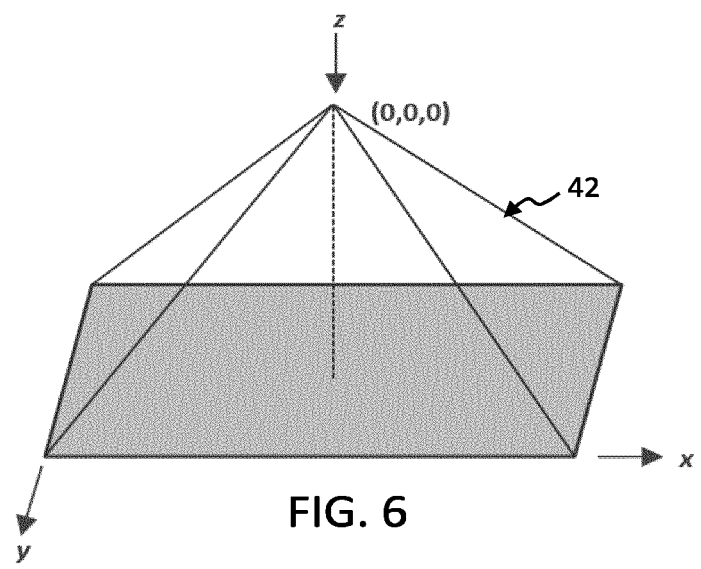
FIG. 6 illustrates a further example first FOV.
Figure 7:
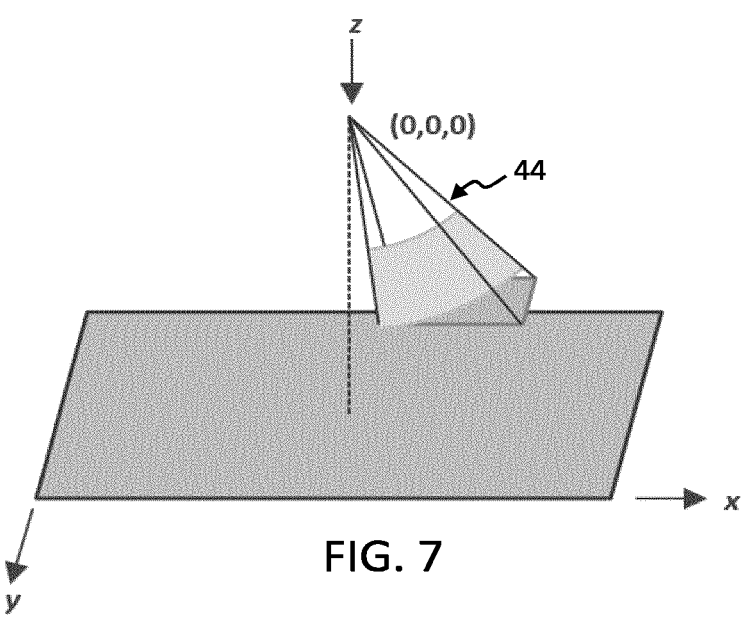
FIG. 7 illustrates a further example adjusted FOV.

By way of further schematic illustration. FIG. 6 shows a further example first FOV 42, the data for which forms an example reference ultrasound dataset. FIG. 7 shows a further example adjusted FOV 44, having a shape configured according to a defined volumetric region within the first FOV. As shown, in this example, the shape is a contorted pyramid shape.

Figure 8:
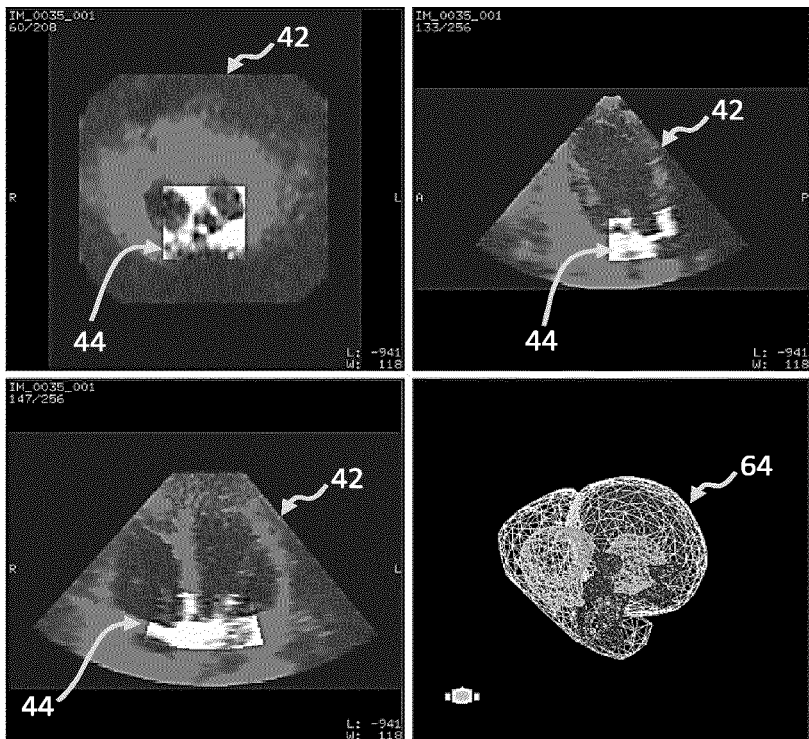
FIG. 8 illustrates the image data acquired across an adjusted FOV relative to a broader first FOV.

FIG. 8 illustrates the adjusted FOV 44 from different angles within the context of the first FOV 42. As can be seen, the adjusted FOV 44 in this case is smaller than the original FOV 42.

As mentioned above, the volumetric region 52 may be defined based on the result of anatomical segmentation applied to the reference ultrasound data. The volumetric region may simply be defined as the volume which is occupied by a detected anatomical feature or object, i.e. the boundaries of the volumetric region are set to match the boundaries of the detected anatomical object. In some other examples, the volumetric region may be set as a shape template which is sized and positioned to encompass the volume occupied by the detected anatomical object. The latter may be computationally more efficient, since it may allow for some of the scan line depth calculations to be performed partially in advance for instance.

Thus, by way of further explanation, in accordance with an advantageous set of embodiments, the method comprises applying segmentation to the reference 3D ultrasound data to detect boundaries of an anatomical object-of-interest in the reference 3D ultrasound data, and further comprises defining the volumetric region within the anatomical region in dependence upon the detected boundaries of the anatomical object-of-interest, wherein the volumetric region is defined so as to at least fully contain the detected boundaries of the anatomical object of interest.

For example, the segmentation may comprise application of a model-based segmentation operation, and/or a machine-learning based segmentation. The output of the segmentation may be a mesh comprising connected vertices which define outer boundaries of a segmented object-of-interest. An example output segmentation mesh 64 is shown in FIG. 8 (bottom right). In this example, the anatomical object-of-interest is the heart.

With regards to implementation of model-based segmentation, various segmentation algorithms are known in the art.

Reference is made for example to the following paper which outlines one example segmentation algorithm: Olivier Ecabert et al. Automatic model-based segmentation of the heart in CT images. IEEE Trans. Medical Imaging, 27 (9): 1189-1201, September 2008.

Reference is further made to the following paper which outlines a further example segmentation algorithm: Olivier Ecabert et al. Segmentation of the heart and great vessels in CT images using a model-based adaptation engine. Medical Image Analysis, 15 (6): 863-876, 2011.

In some examples, the volumetric region 52 is defined so as to fully contain the detected boundaries of the anatomical object of interest, in addition to a pre-defined spacing around the object boundaries, for example for accommodating motion of the object. For example, at least the new 3D ultrasound data acquired with the adjusted FOV may in fact be 4D ultrasound data, comprising a plurality of frames of 3D ultrasound data. Thus, movement of the object may occur, for example if the object exhibits cyclical motion, e.g. the heart or the lungs.

In some examples, defining the volumetric region may comprise defining a 3D shape for said volumetric region, and wherein the 3D shape contains the anatomical object of interest. To relate the volumetric region to the anatomical object of interest, the method may further comprise defining a scale size of said shape which is the minimum able to accommodate the boundaries of the anatomical object of interest, and optionally in addition to said defined spacing around the boundaries (for accommodating movement).

There are different ways to define the 3D shape of the volumetric region. These will be explained in more detail to follow.

The 3D shape of the volumetric region may be defined according to a pre-defined shape template. By way of non-limiting example, the pre-defined shape template may be one of: a cylinder, a cuboid, an ellipsoid, pyramidal shape, truncated or frustrated pyramidal shape, elliptically cylindrical or any other 3D shape.

In further examples, the method further comprises determining a custom shape based on the detected boundaries of the object. For example, defining the shape may comprise determining a custom shape based on the detected boundaries of the object. The custom shape may be a convex hull. For example, the detecting the boundaries of the anatomical object comprises detecting segmentation mesh vertex points which span the boundaries of the object, or comprises detecting pixels which span the boundaries of the object, and wherein the convex hull is defined to connect said vertex points or pixels. This effectively results in a volumetric region with boundaries which match (as closely as possible) the boundaries of the detected anatomical object of interest.

As noted above, a technical advantage of the FOV adaptation method according to embodiments of the present invention is that it enables improved frame rate in 4D imaging by minimizing the size of the 3D FOV without risking excluding important anatomical details.

Thus, in some embodiments, the adjusted 3D FOV 44 may be set to be smaller in volume than the first 3D FOV, and wherein the method further comprises increasing an acquisition frame rate of the 4D ultrasound data after the FOV has been adjusted.

By way of further illustration of the invention, a further example implementation, in accordance with at least one set of embodiments, will now be described in detail. For illustration, this is described with reference to 4D ultrasound imaging of the heart. However, the same principles can be applied to imaging of any anatomical object or region of interest, and 4D imaging is not essential.

In this embodiment. 3D anatomical intelligence is used to compute a volumetric region, acquired with a computed 3D scanning pattern, which is the smallest sufficient needed to capture an anatomical region of interest. This allows, in the context of 4D imaging, highest possible frame rates. It allows, for example, to avoid (error prone) extraction of 3D information from 2D image data.

The method flow according to this embodiment is in accordance with the outline already provided above, and described with reference to FIGS. 2-5. In summary, the method flow is as follows.

As a first step, a first 3D ultrasound image of the heart is acquired. This may for example use a standard or default FOV geometry, e.g. with a cone or pyramid shaped FOV. This forms reference 3D ultrasound data.

The reference 3D ultrasound image is then processed with a segmentation operation to derive anatomical context. This may for example comprise application of a model-based segmentation, or a deep-learning-based artificial neural network. The output of the segmentation may for example be a labelled segmentation mesh comprising connected vertices which together span an outer boundary of an anatomical object-of-interest, i.e. the heart in this case. In further examples, the output may be a segmentation mask which defines one or more pixels lines and/or surfaces within the reference 3D image which represent the boundaries of the object-of-interest.

Neural networks for generic 2D or 3D image segmentation (voxel classification/labelling) are known in the art.

Using the mesh or the mask, a 3D volumetric region is then defined which contains within it all heart structures for which imaging data is desired, and optionally also a further margin to cover heart motion over the cardiac cycle, i.e. heartbeat to heartbeat. Such margins can also ensure that the target structures are imaged with some spatial anatomical context.

This can be achieved for example by processing all vertices of the mask, or all voxels of the mask, and recording the corresponding scan angles $(\theta, \phi)$ relative to the z-axis at which the vertex of each voxel lies. From this, a minimum scan width $\Delta\phi$ which needs to be spanned by the series of scan planes in order to capture all vertices or voxels can be determined. In addition, a minimum required width $\Delta\theta$ of each plane needed to include all vertices or voxels can be determined. Scan lines outside of these angular widths may be deactivated, i.e. not subsequently used in data acquisition.

Furthermore, from the recorded scan angle values of each vertex or voxel, a 3D volumetric region can be defined relative to the ultrasound apparatus co-ordinate system $(d, \theta, \phi)$ which contains the whole of the detected boundary of the anatomical object of interest. For example, a standard 3D shape such as a circular, elliptic, or rectangular angular region can be determined, or a custom shape can be defined, e.g. a convex hull which connects the vertex points of the boundary mesh or the voxels/pixels of the boundary mask.

It is noted that the resulting angular region of the adjusted 3D FOV can be wider that the first FOV of the reference scan or may be less wide. For example, if certain portions of the target anatomical object were not fully covered in the first FOV, then the adjusted FOV can be larger. In other cases, the adjusted FOV may be smaller than the first FOV. Most generally, the adjusted FOV will overlap with the first FOV.

In a next step, the required scan depth for each scan line which has a scan angle within the planned maximum angular ranges $\Delta\phi$. $\Delta\theta$ of the adjusted FOV are computed. For each scan line (i.e., each scan angle $\theta, \phi$), the method comprises determining a distance, along a length of the line, between the ultrasound source and a boundary of the volumetric region defined previously (where this is either defined by a boundary of the anatomical structure itself (possibly plus a defined margin around it), or a shape which contains the structure, as described above).

For example, if the output of the segmentation is represented as a triangle mesh, the volumetric region might be defined so as to have a boundary which matches the shape of the defined mesh. Thus, to determine the scan depths for each scan line, the method may comprise determining all triangles of the mesh boundary structure that are intersected by a scan line and calculate the distance of the relevant intersection point. If the segmentation is instead represented as voxel mask, the method may comprise determining all voxels of the mask that are intersected by a scan line and calculating the distance along the scan line from the ultrasound source to the respective voxel (for instance either to voxel center or most distal corner of the voxel).

For a given scan line, if it intersects the volumetric region boundary at more than one point, the furthest intersection point is used. This results in a set of intersection point co-ordinates for each scan line.

Figure 9:
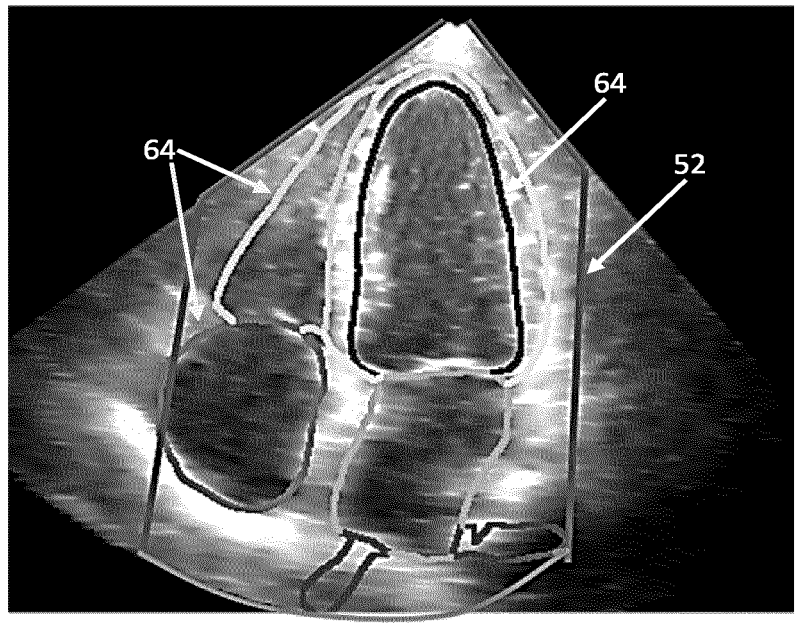
FIG. 9 illustrates one example volumetric region defined according to a shape template sized to be the minimum able to accommodate segmented boundaries of an anatomical object of interest.

By way of illustration. FIG. 9 shows a slice through a volumetric ultrasound dataset. The image illustrates an example set of segmentation boundaries 64 for the heart, and also shows a boundary of a defined volumetric region 52 which contains the whole of the heart.

Figure 10:
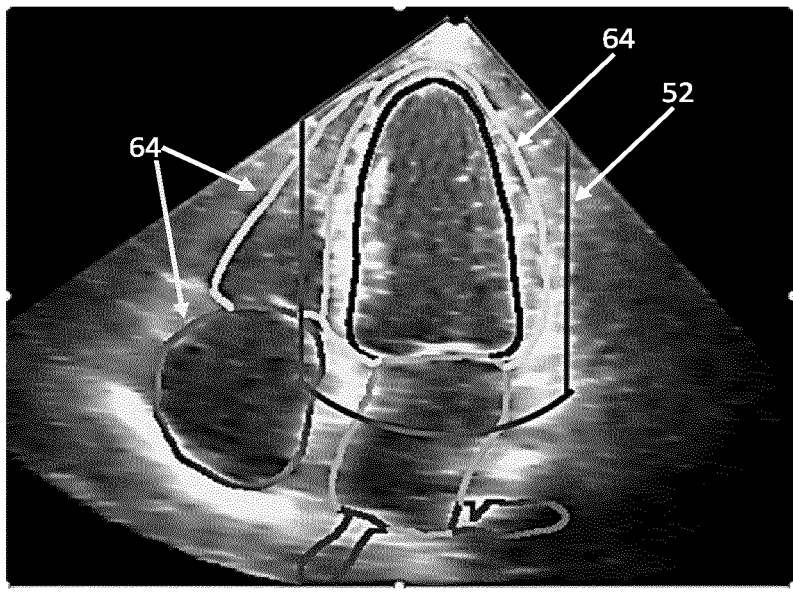
FIG. 10 illustrates a further example volumetric region defined to encompass a subregion of a segmented anatomical object.

FIG. 10 shows a further example, in which the anatomical object-of-interest is instead just a portion of the heart (the left ventricle). The boundaries of the whole heart 64 may be segmented, and a volumetric region 52 has then been defined which covers just the anatomical object/region of interest (i.e. the left ventricle).

As mentioned above, in some examples, the adjusted 3D FOV 44 includes a margin or spacing area around a detected anatomical object. The defined margin or spacing around the anatomical object may be pre-defined, it may be based on a user-input, or, if the acquired reference ultrasound data is 4D ultrasound data, then it may be determined from a detected motion pattern of the object over the series of frames. In other words, an extent of the spacing around the boundaries can be determined based on detecting a maximal extent of the object-of-interest boundary across the series of frames.

After setting the adjusted 3D FOV, new 3D ultrasound data can be acquired. This may be 4D ultrasound data comprising a series of frames of 3D ultrasound data. Areas outside of the adjusted FOV (i.e. beyond the newly set lengths/depths of the scan lines) are not scanned. In other words, each beam (scan line) is only acquired up to the designed scan line depth for that scan line. In this way, higher frame rates are enabled.

The method may further comprise controlling a display of a user interface to display a visual representation of the new acquired image data. Therefore, the adapted field of view is directly visible.

In some embodiments, the user interface may be used to generate a user alert if a currently set FOV does not cover a pre-defined anatomical object or region of interest. The user may manually trigger the FOV adjustment method to adapt the FOV to the anatomical object. If, upon execution of the method, the current FOV is in fact adequate, a hint might be provided to the user that the ultrasound transducer unit positioning needs to be adjusted.

A further aspect of the invention provides a computer program product comprising code means configured, when executed on a processor which is communicatively coupled with an ultrasound imaging apparatus, to cause the processor to perform a method in accordance with any of the examples or embodiments outlined above, or in accordance with any claim of this application.

As briefly outlined above with reference to FIG. 1, another aspect of the invention provides a system 10 comprising: an ultrasound imaging apparatus 30; and a processing arrangement adapted to carry out a method in accordance with any of the examples or embodiments outlined above. The processor is communicatively coupled with the ultrasound imaging apparatus for receiving ultrasound image data and for communicating the adjusted scanning parameters to the ultrasound imaging apparatus.

Figure 11:
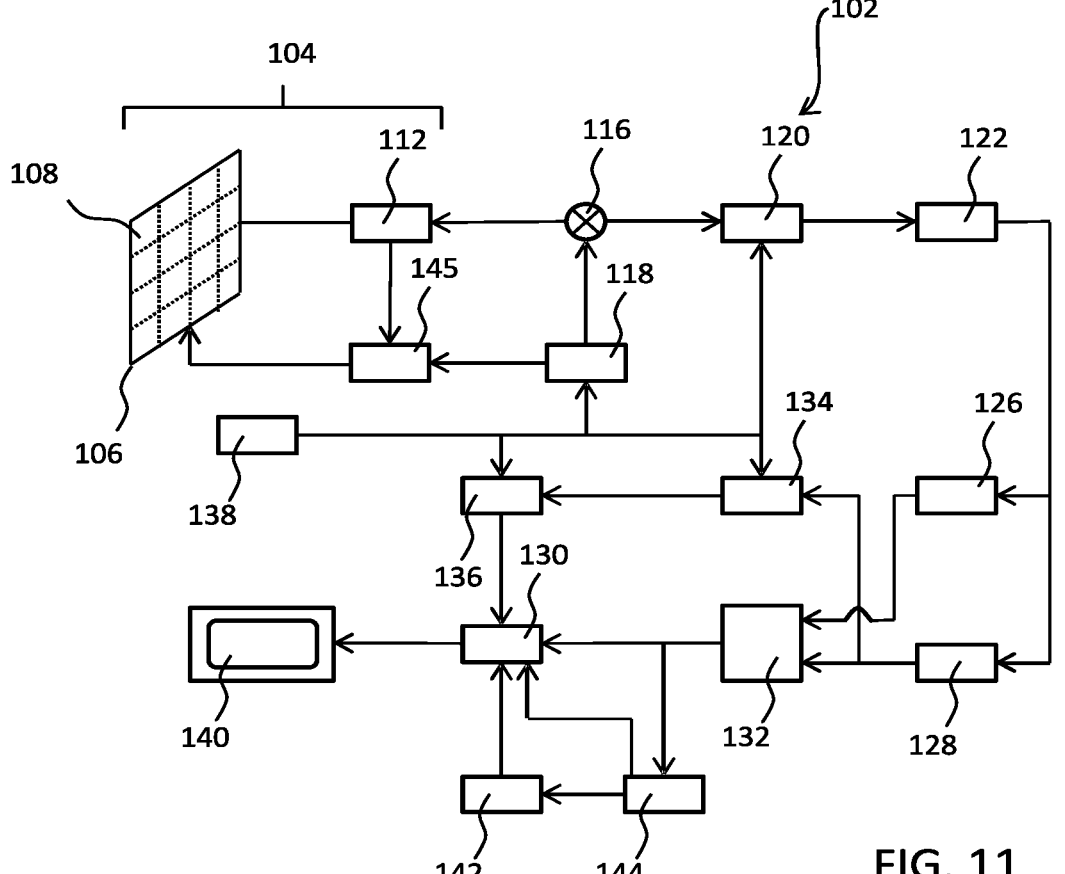
FIG. 11 outlines a block diagram of components of an exemplary ultrasound imaging apparatus.

By way of further, more detailed explanation, the general operation of an exemplary ultrasound imaging apparatus will now be described, with reference to FIG. 11.

The apparatus comprises an array transducer probe 104 which has a transducer array 106 for transmitting ultrasound waves and receiving echo information. The transducer array 106 may comprise CMUT transducers: piezoelectric transducers, formed of materials such as PZT or PVDF: or any other suitable transducer technology. In this example, the transducer array 106 is a two-dimensional array of transducers 108 capable of scanning either a 2D plane or a three dimensional volume of a region of interest. In another example, the transducer array may be a 1D array.

The transducer array 106 is coupled to a microbeamformer 112 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is in general entirely optional. Further, the apparatus includes a transmit/receive (T/R) switch 116, which the microbeamformer 112 can be coupled to and which switches the array between transmission and reception modes, and protects the main beamformer 120 from high energy transmit signals in the case where a microbeamformer is not used and the transducer array is operated directly by the main system beamformer. The transmission of ultrasound beams from the transducer array 106 is directed by a transducer controller 118 coupled to the microbeamformer by the T/R switch 116 and a main transmission beamformer (not shown), which can receive input from the user's operation of the user interface or control panel 138. The controller 118 can include transmission circuitry arranged to drive the transducer elements of the array 106 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 118 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the apparatus for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 118 can be coupled to control a DC bias control 145 for the transducer array. The DC bias control 145 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 112 and are then passed to a main receive beamformer 120 where the partially beamformed signals from individual patches of transducers are combined into a fully beamformed signal, referred to as radio frequency (RF) data. The beamforming performed at each stage may be carried out as described above, or may include additional functions. For example, the main beamformer 120 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 122. The signal processor 122 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 11 only the receiver beamformers 112, 120 are shown, for simplicity. In the complete system, there will also be a transmission chain with a transmission micro beamformer, and a main transmission beamformer.

The function of the micro beamformer 112 is to provide an initial combination of signals in order to decrease the number of analog signal paths. This is typically performed in the analog domain.

The final beamforming is done in the main beamformer 120 and is typically after digitization.

The transmission and reception channels use the same transducer array 106 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 126 and a Doppler processor 128. The B mode processor 126 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 128 processes temporally distinct signals arising from tissue movement and blood flow for the detection of moving substances, such as the flow of blood cells in the image field. The Doppler processor 128 typically includes a wall filter with parameters set to pass or reject echoes returned from selected types of materials in the body.

The structural and motion signals produced by the B mode and Doppler processors are coupled to a scan converter 132 and a multi-planar reformatter 144. The scan converter 132 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 140. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multi-planar reformatter 144, and volume renderer 142 to an image processor 130 for further enhancement, buffering and temporary storage for optional display on an image display 140. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 128 and tissue structure information produced by the B mode processor 126 are coupled to a quantification processor 134. The quantification processor produces measures of different flow conditions such as the volume rate of blood flow in addition to structural measurements such as the sizes of organs and gestational age. The quantification processor may receive input from the user control panel 138, such as the point in the anatomy of an image where a measurement is to be made.

Output data from the quantification processor is coupled to a graphics processor 136 for the reproduction of measurement graphics and values with the image on the display 140, and for audio output from the display device 140. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 138, such as patient name. The user interface is also coupled to the transmit controller 118 to control the generation of ultrasound signals from the transducer array 106 and hence the images produced by the transducer array and the ultrasound imaging apparatus. The transmit control function of the controller 118 is only one of the functions performed. The controller 118 also takes account of the mode of operation (given by the user) and the corresponding required transmitter configuration and band-pass configuration in the receiver analog to digital converter. The controller 118 can be a state machine with fixed states.

The user interface is also coupled to the multi-planar reformatter 144 for selection and control of the planes of multiple multi-planar reformatted (MPR) images which may be used to perform quantified measures in the image field of the MPR images.

Embodiments of the invention described above employ a processing arrangement. The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented. The processing arrangement includes a communication module or input/output for receiving data and outputting data to further components.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A computer-implemented method, comprising:
obtaining reference 3D ultrasound data of an anatomical region for a first 3D field of view, FOV, wherein the reference ultrasound data comprises data for a series of scan lines, each scan line having a scan angle along a first ($) and second ($\theta$) angular scan direction, and maximum scan depth (d) along a direction of the scan line;
applying segmentation to the reference 3D ultrasound data to detect boundaries of an anatomical object-of-interest in the reference 3D ultrasound data;
defining a volumetric region within the anatomical region, the volumetric region having one or more boundaries, wherein the volumetric region is defined in dependence upon the detected boundaries of the anatomical object-of-interest, and wherein the volumetric region is defined so as to fully contain the detected boundaries of the anatomical object-of-interest;
adjusting one or more scanning parameters to acquire new 3D ultrasound data with an adjusted 3D FOV, wherein adjusting the scanning parameters is performed in dependence upon the boundaries of the volumetric region, and wherein the adjusted 3D FOV fully encompasses the volumetric region, and wherein adjusting the scanning parameters comprises adjusting the maximum scan depth (d) of each individual scan line, and
acquiring new 3D ultrasound data for the adjusted 3D FOV using the adjusted scanning parameters.

2. The method of claim 1, wherein the adjusting the maximum scan depth (d) of each individual scan line comprises adjusting a time duration of a receive phase of a transmit/receive sequence of one or more transducers used to acquire the relevant scan line.

3. The method of claim 1, wherein the scanning parameters are adjusted to define a set of scan lines having scan depths (d) set such that each scan line terminates at a point of intersection of the scan line with a distal-most one of the one or more boundaries of the defined volumetric region.

4. The method of claim 3, further comprising identifying a subset of scan lines which do not intersect with the defined volumetric region and wherein the subset of scan lines which do not intersect are deactivated when scanning the adjusted 3D FOV.

5. The method of claim 3, wherein the adjusted 3D FOV includes a subset of scan lines which do not intersect the volumetric region, and wherein the maximum scan depth (d) for each of said subset of scan lines is set based on a scan depth which has been set for a nearest scan line which does intersect the volumetric region.

6. The method of claim 1, wherein:
the scan lines in each of the reference and new 3D ultrasound data span each of a series of 2D scan planes, wherein the series of 2D planes together span the respective 3D FOV across the first angular direction ($\phi$), and the scan lines forming each plane span the plane across the second angular direction ($\theta$), and each 2D scan plane having an angular orientation ($\phi_j$) along said first angular direction, and
wherein adjusting the scan parameters further comprises:
adjusting for each individual 2D scan plane, a maximum angular width ($\Delta\theta$) along said second angular direction spanned by the scan lines in the 2D plane, and
adjusting a maximum angular width ($\Delta\phi$) along said first angular direction spanned by the series of scan planes.

7. The method of claim 6, wherein, for each 2D scan plane,
the maximum angular width ($\Delta\theta$) is set to the minimum width required for said 2D scan plane to fully encompass the boundaries of the volumetric region; or
the maximum angular width ($\Delta\theta$) is set to a sum of: the minimum width required for said plane to fully encompass the boundaries of the volumetric region, and a defined angular margin.

8. The method of claim 1, wherein:
the boundaries of the volumetric region are set as the boundaries of the anatomical object-of-interest.

9. The method of claim 1, wherein defining the volumetric region comprises defining a 3D shape for said volumetric region, and defining a scale size of said shape which is the minimum able to accommodate the boundaries of the anatomical object-of-interest, and optionally in addition to a defined spacing around the boundaries.

10. The method of claim 9, wherein defining the 3D shape of the volumetric region comprises:
defining the shape according to a pre-defined shape template, for example a cylinder, a cuboid, an ellipsoid, a pyramid, a truncated pyramid, or an elliptical cylinder; or
determining a custom shape based on the detected boundaries of the object.

11. The method of claim 10, wherein the defining the shape comprises determining a custom shape based on the detected boundaries of the object, and wherein the custom shape is a convex hull.

12. The method of claim 11, wherein the detecting the boundaries of the anatomical object-of-interest comprises detecting segmentation mesh vertices which span the boundaries of the object, or comprises detecting voxels which span the boundaries of the object, and wherein the convex hull is defined to connect said vertices or voxels.

13. The method of claim 1, wherein the reference ultrasound data is 4D ultrasound data, comprising a series of frames of 3D ultrasound data.

14. The method of claim 13, wherein the volumetric region is defined so as to fully contain the detected boundaries of the anatomical object-of-interest in addition to a pre-defined spacing around the object boundaries; and wherein an extent of said spacing around the boundaries is determined based on detecting a maximal extent of the object-of-interest boundary across the series of frames.

15. A non-transitory computer readable medium comprising code that in response to execution on on a processor communicatively coupled with an ultrasound imaging apparatus, cause the processor to perform a method in accordance with claim 1.

16. An apparatus comprising:

an input/output for two-way communication with an ultrasound imaging apparatus; and one or more processors, adapted to:

obtain at the input/output reference 3D ultrasound data of an anatomical region for a first 3D field of view, FOV, wherein the reference ultrasound data comprises data for a series of scan lines, each scan line having a scan angle along a first ($) and second ($\theta$) angular scan direction, and maximum scan depth (d) along a direction of the scan line;

apply segmentation to the reference 3D ultrasound data to detect boundaries of an anatomical object-of-interest in the reference 3D ultrasound data;

define a volumetric region within the anatomical region, the volumetric region having one or more boundaries, wherein the volumetric region is defined in dependence upon the detected boundaries of the anatomical object-of-interest, and wherein the volumetric region is defined so as to fully contain the detected boundaries of the anatomical object-of-interest;

adjust one or more scanning parameters to acquire new 3D ultrasound data with an adjusted 3D FOV, wherein adjusting the scanning parameters is performed in dependence upon the boundaries of the volumetric region, and wherein the adjusted 3D FOV fully encompasses the volumetric region, and wherein adjusting the scanning parameters comprises adjusting the maximum scan depth (d) of each individual scan line, and communicate the adjusted scanning parameters to the ultrasound imaging apparatus to cause the apparatus to acquire new 3D ultrasound data for the adjusted 3D FOV using the adjusted scanning parameters.

17. An ultrasound system apparatus comprising:

an ultrasound imaging apparatus and an input/output for two-way communication with the ultrasound imaging apparatus; and one or more processors, adapted to:

obtain at the input/output reference 3D ultrasound data of an anatomical region for a first 3D field of view, FOV, wherein the reference ultrasound data comprises data for a series of scan lines, each scan line having a scan angle along a first ($\theta$) and second ($\theta$) angular scan direction, and maximum scan depth (d) along a direction of the scan line;

apply segmentation to the reference 3D ultrasound data to detect boundaries of an anatomical object-of-interest in the reference 3D ultrasound data;

define a volumetric region within the anatomical region, the volumetric region having one or more boundaries, wherein the volumetric region is defined in dependence upon the detected boundaries of the anatomical object-of-interest, and wherein the volumetric region is defined so as to fully contain the detected boundaries of the anatomical object-of-interest;

adjust one or more scanning parameters to acquire new 3D ultrasound data with an adjusted 3D FOV, wherein adjusting the scanning parameters is performed in dependence upon the boundaries of the volumetric region, and wherein the adjusted 3D FOV fully encompasses the volumetric region, and wherein adjusting the scanning parameters comprises adjusting the maximum scan depth (d) of each individual scan line, and communicate the adjusted scanning parameters to the ultrasound imaging apparatus to cause the apparatus to acquire new 3D ultrasound data for the adjusted 3D FOV using the adjusted scanning parameters.

\* \* \* \* \*